United States Patent
Seiler

(10) Patent No.: US 10,390,956 B2
(45) Date of Patent: Aug. 27, 2019

(54) DEVICE FOR COVERING AND/OR RECONSTRUCTING A BONE DEFECT SITE, METHOD FOR PRODUCING A CAP FOR A COVER FOR A BONE DEFECT SITE

(71) Applicant: ReOss GmbH, Filderstadt (DE)

(72) Inventor: Marcus Seiler, Stuttgart (DE)

(73) Assignee: ReOss GmbH, Filderstadt (DE)

(*) Notice: Subject to any disclaimer, the term of this patent is extended or adjusted under 35 U.S.C. 154(b) by 60 days.

(21) Appl. No.: 15/572,249

(22) PCT Filed: May 9, 2016

(86) PCT No.: PCT/DE2016/000207
§ 371 (c)(1),
(2) Date: Nov. 7, 2017

(87) PCT Pub. No.: WO2016/180397
PCT Pub. Date: Nov. 17, 2016

(65) Prior Publication Data
US 2018/0104060 A1    Apr. 19, 2018

(30) Foreign Application Priority Data

May 8, 2015 (DE) .................. 10 2015 006 154
Jan. 11, 2016 (DE) .................. 10 2016 000 235

(51) Int. Cl.
A61F 2/28     (2006.01)
A61F 2/30     (2006.01)

(52) U.S. Cl.
CPC ........ *A61F 2/2846* (2013.01); *A61F 2/30942* (2013.01); *A61F 2002/30062* (2013.01);
(Continued)

(58) Field of Classification Search
CPC .......... A61F 2/28; A61F 2/2846; A61B 17/82; A61B 17/80
See application file for complete search history.

(56) References Cited

U.S. PATENT DOCUMENTS 4,816,339 A   3/1989   Tu et al.
5,741,257 A   4/1998   Kirsch
(Continued)

FOREIGN PATENT DOCUMENTS

DE    42 26 465 A1    2/1993
DE    43 02 708 C2    8/1994
(Continued)

OTHER PUBLICATIONS

Response to European Patent Office by German patent attorneys regarding PCT/DE2016/000207 dated May 5, 2017 with English translation of relevant parts.
(Continued)

*Primary Examiner* — Jason-Dennis N Stewart
(74) *Attorney, Agent, or Firm* — Collard & Roe, P.C.

(57) ABSTRACT

A device for covering and/or reconstructing a bone defect site includes a cap (molded shell, rigid shell, molded body) having a rim and at least one fixing device for fixing the cap on a bone. The cap has a dimensionally stable (rigid) nature. A wall of the cap facing the bone defect or a wall of the cap facing away from the bone defect corresponds to the shape of the regenerated bone, at least one positioning device being located on the rim of the cap. A method produces a cap for a covering device for a bone defect site.

32 Claims, 9 Drawing Sheets

Figure 1:
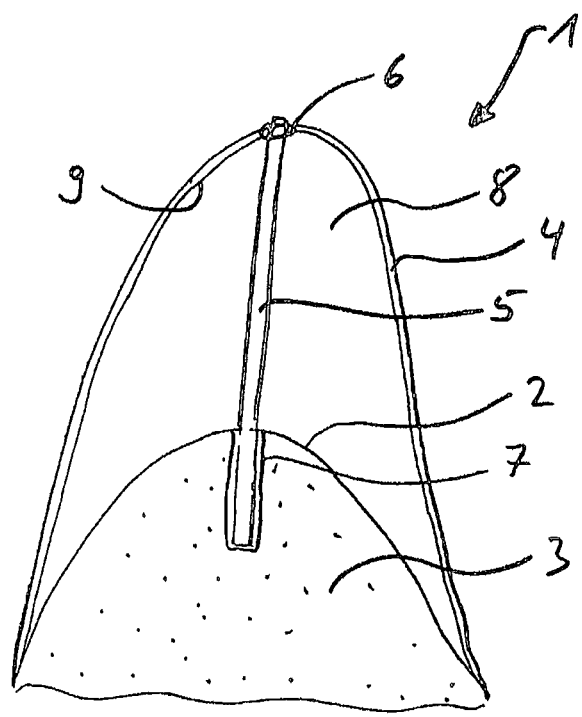

(52) U.S. Cl.
CPC ............ *A61F 2002/30324* (2013.01); *A61F 2002/30561* (2013.01); *A61F 2002/30576* (2013.01); *A61F 2002/30784* (2013.01)

(56) References Cited

U.S. PATENT DOCUMENTS

| | | | |
|---|---|---|---|
| 5,824,088 | A | 10/1998 | Kirsch |
| 5,976,140 | A | 11/1999 | Haas |
| 5,984,966 | A | 11/1999 | Kiema et al. |
| 7,172,422 | B1 | 2/2007 | Essiger |
| 9,017,406 | B2 | 4/2015 | Seiler |
| 2004/0024466 | A1 | 2/2004 | Heerklotz et al. |
| 2004/0138591 | A1 | 7/2004 | Iseki et al. |
| 2004/0143344 | A1 | 7/2004 | Malaviya et al. |
| 2006/0094951 | A1 | 5/2006 | Dean et al. |
| 2008/0177334 | A1 | 7/2008 | Stinnette |
| 2009/0234459 | A1 | 9/2009 | Sporring et al. |
| 2011/0151400 | A1 | 6/2011 | Boiangiu et al. |

FOREIGN PATENT DOCUMENTS

| | | |
|---|---|---|
| DE | 195 20 864 A1 | 12/1996 |
| DE | 198 30 992 A1 | 1/2000 |
| DE | 10 2005 039 382 B4 | 2/2007 |
| DE | 10 2005 041 412 A1 | 3/2007 |
| DE | 10 2005 060 761 A1 | 6/2007 |
| DE | 10 2006 047 054 A1 | 4/2008 |
| DE | 10 2011 011191 A1 | 8/2011 |
| EP | 0 809 979 A1 | 12/1997 |
| EP | 2 737 871 A2 | 6/2014 |
| WO | 96/12446 A1 | 5/1996 |
| WO | 00/59409 A1 | 10/2000 |
| WO | 01/91818 A1 | 12/2001 |
| WO | 2006/051401 A2 | 5/2006 |
| WO | 2010/019463 A1 | 2/2010 |

OTHER PUBLICATIONS

International Search Report of PCT/DE2016/000207, dated Aug. 25, 2016.
International Search Report of PCT/DE2011/000131, dated Jun. 21, 2011.
English translation of International Preliminary Report on Patentability and Written Opinion of the International Searching Authority in PCT/DE2011/000131, dated Aug. 21, 2012.

DEVICE FOR COVERING AND/OR RECONSTRUCTING A BONE DEFECT SITE, METHOD FOR PRODUCING A CAP FOR A COVER FOR A BONE DEFECT SITE

CROSS REFERENCE TO RELATED APPLICATIONS

This application is the National Stage of PCT/DE2016/000207 filed on May 9, 2016, which claims priority under 35 U.S.C. § 119 of German Application Nos. 10 2015 006 154.2 filed on May 8, 2015, and 10 2016 000 235.2 filed on Jan. 11, 2016, the disclosure of which is incorporated by reference. The international application under PCT article 21(2) was not published in English.

STATE OF THE ART

The invention relates to a device for covering and/or reconstruction of a bone defect site in accordance with the preamble of claim 1, and to a method for production of a cap of a covering device for a bone defect site in accordance with the preamble of claim 20.

Bone defect sites in the form of recesses or cavities in endogenous bone tissue are often filled with bone reconstruction material in bone surgery, for example in the reconstruction of bone in orthopedic, neurosurgical or plastic surgery or in the case of gnathic surgery operations. In general, the bone reconstruction material consists of a mixture of synthetic bone replacement material (e.g. hydroxyl apatite granulate) and endogenous bone particles. In order for osseous growth to occur by means of the bone reconstruction material essentially exclusively from the bone side, the recess is closed off with a covering membrane, as described in the patent DE 43 02 708 C2.

The covering membrane is attached, using attachment nails, to the endogenous healthy bone that borders on the bone defect site, which bone is damaged by the attachment nails, with attachment requiring a maximum of skill on the part of the surgeon, since the covering membrane consists of a flexible material.

In order to overcome this disadvantage of a lack of support function of the covering membrane, a covering membrane, which consists of multiple layers, is described in the U.S. Pat. No. 4,816,339, wherein these layers do not consist of a resorbable membrane material. In this regard, it might be necessary for a second surgery to be performed after the bone defect has healed, in order to remove exogenous material.

A biodegradable hollow body, which particularly has a hollow-cylindrical or conical cylindrical shape, is proposed in the patent DE 10 2005 039 382 B4. The hollow body has a plurality of openings in its walls, by means of which absorption of blood and thereby buildup of endogenous bone is possible. It is disadvantageous, in this connection, that a cylindrical bore must be introduced into the existing bone by means of a drill, in order to insert the hollow body.

In the published application DE 10 2006 047 054 A1, an implant bearing is proposed, which is characterized by great fit precision and stability, so that the treating physician can easily handle and implant it. The implant socket, produced from hydroxyl apatite, which has a thin membrane, particularly composed of resorbable material, on the side facing the mucous membrane, for protection of the mucous membrane against mechanical effects and for protection of the implant socket against tissue growing in from the side of the mucous membrane, is produced using a cumulative manufacturing method, so that the material composition forms a "gradient structure" in the sense of a density that particularly decreases toward the inside. In this regard, a construction having a particularly porous structure is provided on the side facing the bone, and a compact construction is provided on the outside of the implant socket, on which a structure for holding a tooth implant and/or a tooth replacement is situated.

Furthermore, devices for a bone defect site are described in the published applications DE 198 30 992 A1, DE 10 2005 060 761 A1, DE 42 26 465 A1, WO 01/91818 A1, DE 10 2005 041 412 A1, DE 10 2006 047 054 A1, US 2011/0151400 A1, WO 00/59409 A1, WO 96/12446 A1, EP 2 737 871 A2, and WO 2006/051401 A2, and the U.S. Pat. No. 7,172,422 B1, with all of these solutions having the disadvantage that they affect the healthy bone present next to the bone defect site.

In order to avoid this disadvantage, a precision-fit covering device is proposed in the published application DE 10 2011 011 191 A1, but this has the disadvantage that its positioning at the bone defect site is made more difficult specifically because of the precise fit.

THE INVENTION AND ITS ADVANTAGES

The device according to the invention for covering and/or reconstruction of a bone defect site, wherein the term "bone defect site" refers to a site of a bone (for example hip, spinal column, head, jaw or the like) (which is diseased, deformed, injured, changed due to aging processes, changed due to degeneration (for example after tooth extraction, tumor, etc.) and/or changed in volume), of a human being or an animal, which site deviates from the shape and/or the volume of a healthy bone, the device having the characteristics according to one aspect of the invention, and the method for production of a cap of a covering device for a bone defect site having the characteristics according to another aspect of the invention, have the advantage, in contrast, that the device for covering and/or reconstruction of a bone defect site can be formed from a cap (for example a molded shell, rigid shell, molded body), which can be structured in one or multiple layers, having a rim and, if applicable, at least one fixation means disposed within the bone defect site, for fixation of the cap on a bone, wherein at least one positioning means is disposed at the rim of the cap, which means is characterized by a dimensionally stable (rigid) composition and stands in contact with the bone, at least in part (at the rim) in the boundary region between the bone defect site and the adjacent healthy bone, and a wall of the cap (in the sense of a surface or side), which faces the bone defect, or a wall of the cap (in the sense of a surface or side), which faces away from the bone defect, corresponds to the shape of the bone regenerated within the bone defect site, which has the shape of a healthy bone once again, due to its regeneration. Positioning of the cap on a healthy bone that borders on the bone defect site is possible by means of the at least one positioning means, since the positioning means has a wall (in the sense of a surface or side) that faces away from the healthy bone and a wall (in the sense of a surface or side) that faces the healthy bone and corresponds to it, at least in part. The cap is exclusively disposed and/or fixed in place in the region of the bone defect site, which is completely or at least partially covered by the cap, so that it does not affect the healthy bone that borders on the bone defect site, at which no regeneration of bone, takes place in any case, because of its health. Instead of only partial covering of the bone defect site by the cap, the cap is therefore preferably coordinated with the bone defect site with a precise fit, and preferably ends flush with the healthy bone. In this way, the bone defect site is completely covered by the cap, which does not project beyond the bone defect site.

According to an advantageous embodiment of the device according to the invention, the cap and/or at least one fixation means and/or at least one positioning means consist(s), at least in part, of a biocompatible material.

According to an additional advantageous embodiment of the device according to the invention, the material is of organic and/or inorganic origin. This can also be an autogenic, syngenic, allogenic, xenogenic, synthetic or alloplastic material.

According to an additional advantageous embodiment of the device according to the invention, the cap and/or at least one fixation means and/or at least one positioning means consist(s), at least in part, of a biodegradable material.

According to an additional advantageous embodiment of the device according to the invention, the cap and/or at least one fixation means and/or at least one positioning means can consist, at least in part, of a resorbable material. It is advantageous that the resorption time of the rigid shell can be controlled by means of its resorption gradient and/or the resorption time can also amount to less than six months, so that the implant can be inserted contemporarily. Preferably, resorbable metals or alloys, particularly magnesium or magnesium alloys, are used. The 3D models (for example the cap and/or the fixation means) are preferably built up using the laser-melting method (laser melting method), under vacuum, with a 3D printer preferably being used.

According to an additional advantageous embodiment of the device according to the invention, the cap and/or at least one fixation means and/or at least one positioning means consist(s), at least in part, of a polymer or a polymer compound.

According to an additional advantageous embodiment of the device according to the invention, the cap and/or at least one fixation means and/or at least one positioning means consist(s), at least in part, of polylactide. Polylactides are composed of many lactic acid molecules bound to one another, and belong to the polymers. The advantage of polylactide plastics, which are also called polylactic acids (PLA), is that they are plastics that can be deformed by means of supplying heat, and that they are biocompatible.

According to an additional advantageous embodiment of the device according to the invention, the cap and/or at least one positioning means has/have a constant or a varying wall thickness.

According to an advantageous embodiment of the device according to the invention in this regard, the wall thickness should amount to at least 0.2 mm, preferably 0.5 mm, but at least so much that dimensional stability of the molded shell or of a positioning means occurs.

According to an additional advantageous embodiment of the device according to the invention, the fixation means is a pin, a screw, a nail and/or a bone adhesive. In order to protect the healthy bone, the fixation means is/are preferably disposed in the region of the bone defect site.

According to an additional advantageous embodiment of the device according to the invention, the cap has at least one milled region (bore for the fixation means).

According to an advantageous embodiment of the device according to the invention in this regard, the milled region corresponds to the fixation means.

According to an additional advantageous embodiment of the device according to the invention, the wall that faces the bone defect has surface conditioning.

According to an advantageous embodiment of the device according to the invention in this regard, the surface can have a micro-structuring, pores, osteoblast attractants, means for promoting bone growth and/or bone replacement material that contains BMP.

According to an additional advantageous embodiment of the device according to the invention, the cap has at least one opening. This means that the cap does not have to have a closed wall. Because of the plurality of openings, the cap can have a net-like structure at least at certain points, with the wall of the net-like structure that faces away from the bone defect or the wall of the net-like structure that faces the bone defect corresponding to the shape of the regenerated bone.

According to an additional advantageous embodiment of the device according to the invention, the cap has at least one planned breaking point. The planned breaking point brings with it the advantage that if the cap is supposed to be removed after successful bone regeneration, this removal can take place in minimally invasive manner, without "having to expose everything," since the cap can be broken down into at least two parts because of the planned breaking point. Removal of the cap (for example after bone regeneration) is therefore very easily possible. Furthermore, the planned breaking point is supposed to serve for separating parts of the cap that are not required from the rest of the cap.

According to an additional advantageous embodiment of the device according to the invention, the cap has at least one attachment device (for example a recess) for at least one implant to be put in place.

According to an advantageous embodiment of the device according to the invention in this regard, at least one attachment device (for example a recess) is covered, at least in part, by a part of the cap that is connected with the remaining part of the cap by means of at least one planned breaking point.

According to an advantageous embodiment of the device according, to the invention in this regard, at least one planned breaking point is disposed between the cap and a positioning means. As a result, the positioning means, which lies on the healthy bone and therefore might ride on it in disruptive manner, for example after fixation of the cap or after regeneration of the bone at the bone defect site, can be removed from the possibly remaining cap.

According to an advantageous embodiment of the method according to the invention for production a cap of a covering device for a bone defect site, in which computer-assisted design (CAD) of the cap is combined with computer-assisted manufacturing (CAM) to produce CAD/CAM, so that a draft model of the cap developed on the computer is directly transmitted to manufacturing electronically, consisting of the following method steps:

recording of a data set that represents the affected bone defect site in its three-dimensionality, by means of tomography or similar imaging methods, use of the data set for planning the cap, which has a wall that faces away from the bone defect and a wall that faces the bone defect, and can be fixed in place on a bone with at least one fixation means, conversion of the planning of the cap to a planning data set, and provision of the planning data set to a computer-assisted manufacturing method, wherein the cap is formed from a dimensionally stable material, and its wall (in the sense of a surface or side) that faces the bone defect, or its wall (in the sense of a surface or side) that faces away from the bone defect corresponds to the shape of the regenerated bone, and recording of the data set, which represents the affected bone defect site in its three-dimensionality, takes place by means of tomography, computer tomography, digital volume tomography, sonography or the like, wherein during and/or after manufacturing of the cap, at least one positioning means is disposed at the rim of the cap, which means serves for positioning of the cap on a healthy bone that borders on the bone defect site, and the one wall (in the sense of a surface or side) that faces away from the healthy bone and a wall (in the sense of a surface or side) that faces the healthy bone and corresponds to it, at least in part, recording of the first data set represents the affected bone defect site in its three-dimensionality and/or recording of the second data set represents the shape of the bone that is still healthy, in its three-dimensionality.

According to an additional advantageous embodiment of the method according to the invention for production of a cap of a covering device for a bone defect site, recording of the first data set, which represents the actual state, and/or recording of the second data set, which represents the reference state, take(s) place by means of at least one imaging method.

According to an additional advantageous embodiment of the method according to the invention for production of a cap of a covering device for a bone defect site, recording of the first data set and/or recording of the second data set take(s) place using at least one method that allows three-dimensional representation of a bone. In particular, recording of the first data set and/or recording of the second data set take(s) place by means of tomography, computer tomography, digital volume tomography, sonography or the like.

According to an additional advantageous embodiment of the method according to the invention for production of a cap of a covering device for a bone defect site, recording of the data set of the healthy bone takes place after the healthy bone has fully grown. In this way, it is possible that if necessary, the ideal state (reference state) of the bone is documented, so that it is known what a bone that might have to be regenerated later looks like. In humans, recording of the data set of the healthy bone should preferably take place at the age of 18 to 25 years. Of course, it is also conceivable that in the fully grown state of the bones, multiple healthy bones or the entire skeleton of the human being or of the animal is recorded, documented and/or stored in memory. It would also be conceivable that a cap is already produced, at least in part, at the time of recording of the healthy bone.

According to an advantageous embodiment of the method according to the invention for production of a cap of a covering device for a bone defect site, in this regard, the data set of the healthy bone is stored (preserved) on a memory medium for later use.

According to an additional advantageous embodiment of the method according to the invention for production of a cap of a covering device for a bone defect site, the cap is formed by means of milling during the manufacturing method.

According to an additional advantageous embodiment of the method according to the invention for production of a cap of a covering device for a bone defect site, at least one attachment device for at least one implant to be set is disposed on the cap during manufacturing of the cap. The attachment device can be structured as a recess, for example.

According to an advantageous embodiment of the method according to the invention for production of a cap of a covering device for a bone defect site, in this regard, at least one attachment device (for example a recess) is exposed by means of removal of part of the cap, which is connected with the remaining part of the cap by means of at least one planned breaking point before removal. In this regard, the time point of exposure of the attachment device can lie before or after placement of the covering device on the bone defect site.

According to an additional advantageous embodiment of the method according to the invention for production of a cap of a covering device for a bone defect site, at least one planned breaking point is placed on the cap during manufacturing of the cap.

According to an additional advantageous embodiment of the method according to the invention for production of a cap of a covering device for a bone defect site, at least one planned breaking point is disposed between the cap and a positioning means.

According to an additional advantageous embodiment of the method according to the invention for production of a cap of a covering device for a bone defect site, a cleaning process and/or sterilization process is carried out during manufacturing of the cap.

According to an additional advantageous embodiment of the method according to the invention for production of a cap of a covering device for a bone defect site, the cap can be used in a device for covering and/or reconstruction of a bone defect site according to one aspect of the invention. As a result, a device for covering and/or reconstruction of a bone defect site can be created, the cap and/or fixation means of which, for example, of an artificial material and/or of a material having an autogenic, synergenic, allogenic or xenogenic origin human and/or animal bone or the human, animal or artificial matrix having a shape by means of which the region situated between the bone and the desired shape of the regenerated bone is completely or almost completely filled. For this purpose, a bone block, for example, is taken from the donor, and this block is subsequently modeled, if necessary, by means of CAD/CAM.

By means of the method according to the invention, a device according to the invention for covering and/or reconstruction of a bone defect site can be created, the cap and/or fixation means of which is/are derived, for example, from a material of organic and/or inorganic origin. This can also be a synthetic material and/or a material of autogenic, synergenic, allogenic and/or xenogenic, alloplastic, human and/or animal origin. In this regard, the human, animal or synthetic matrix can also have a shape by means of which the region situated between the bone and the desired shape of the regenerated bone is completely or almost completely filled. For this purpose, a bone block, for example, is taken from the donor (autologous donor or allogenic donor), and this block is subsequently modeled, if necessary, by means of CAD/CAM.

Further advantages and advantageous embodiments of the invention can be derived from the following description, the drawing, and the claims.

DRAWING

Figure 2:
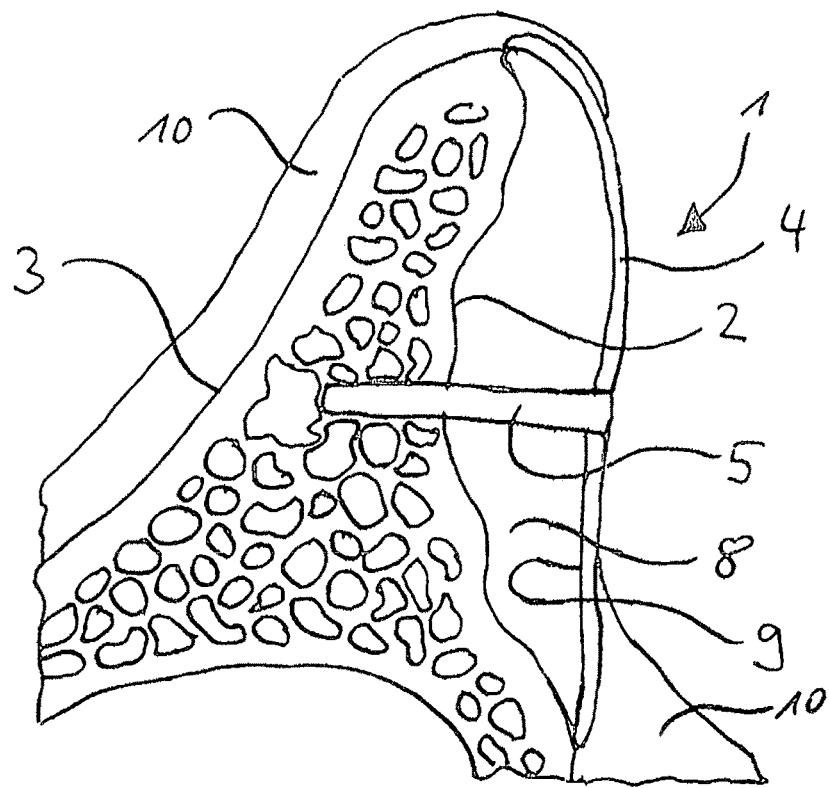
Figure 3:
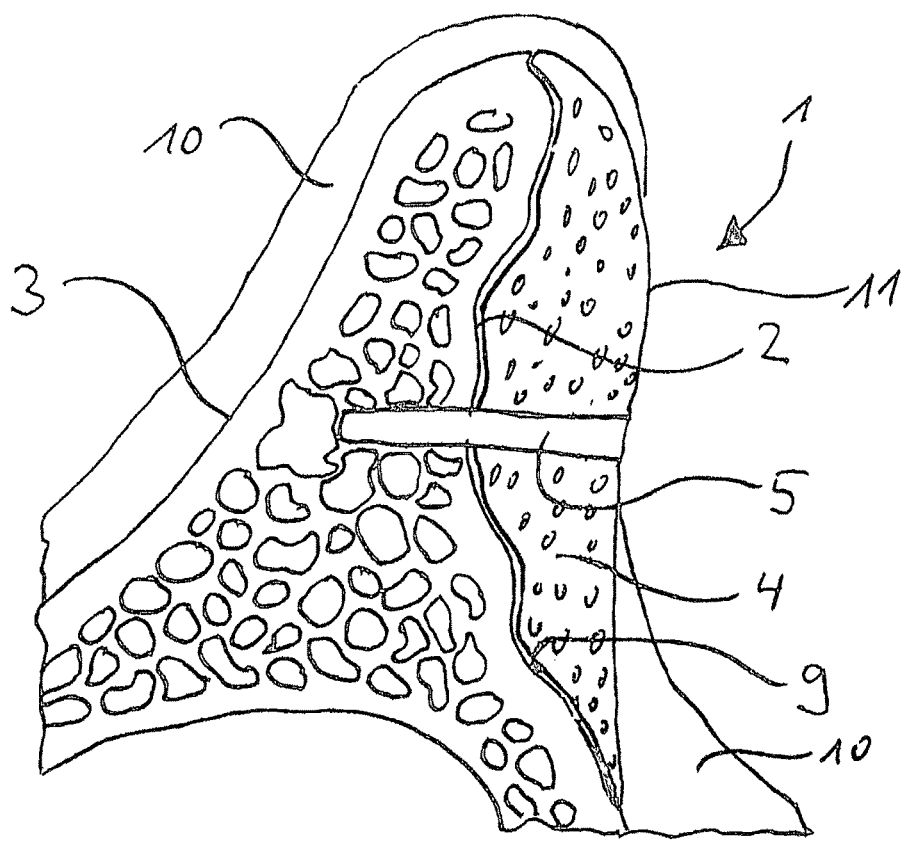
Figure 4:
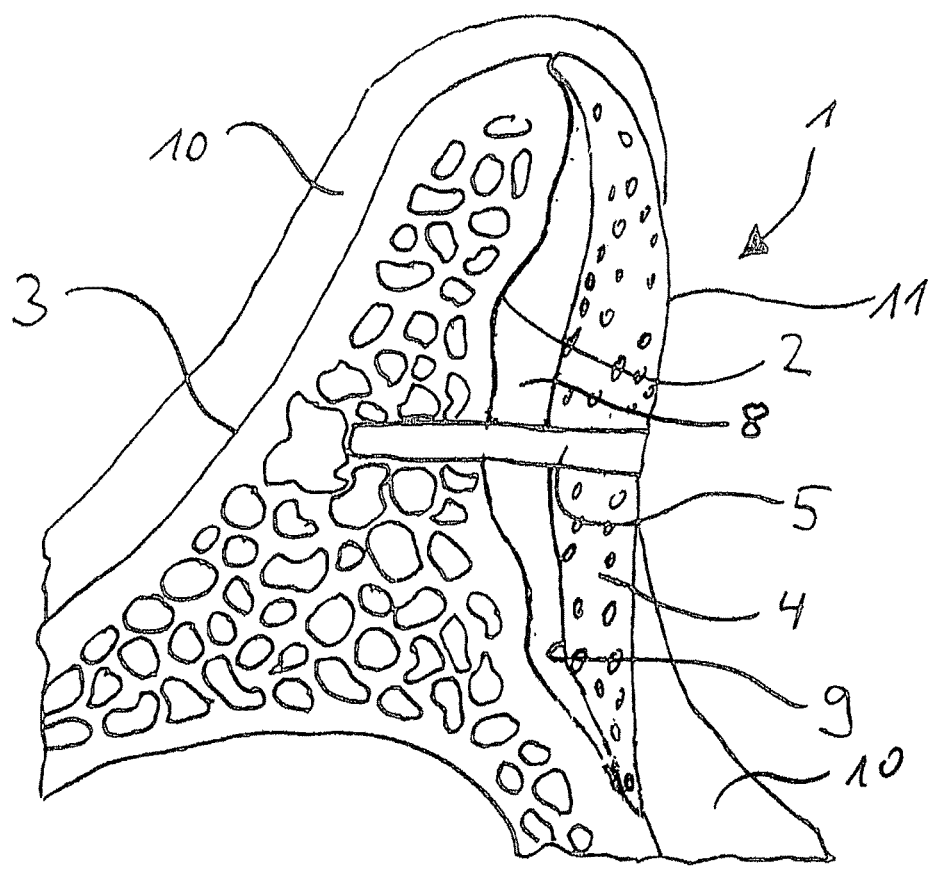
Figure 5:
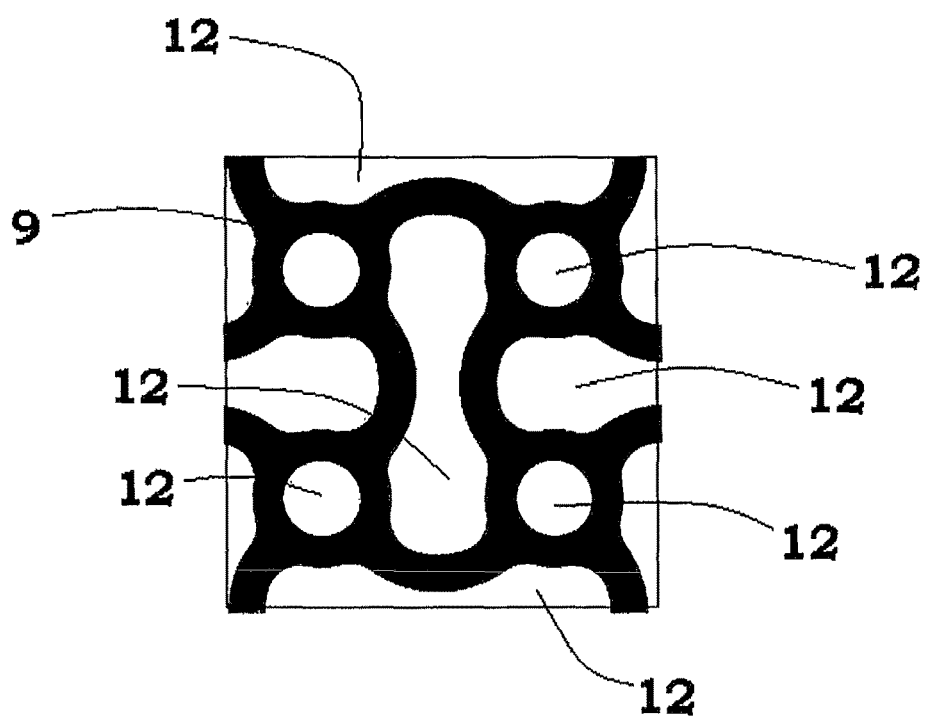
Figure 6:
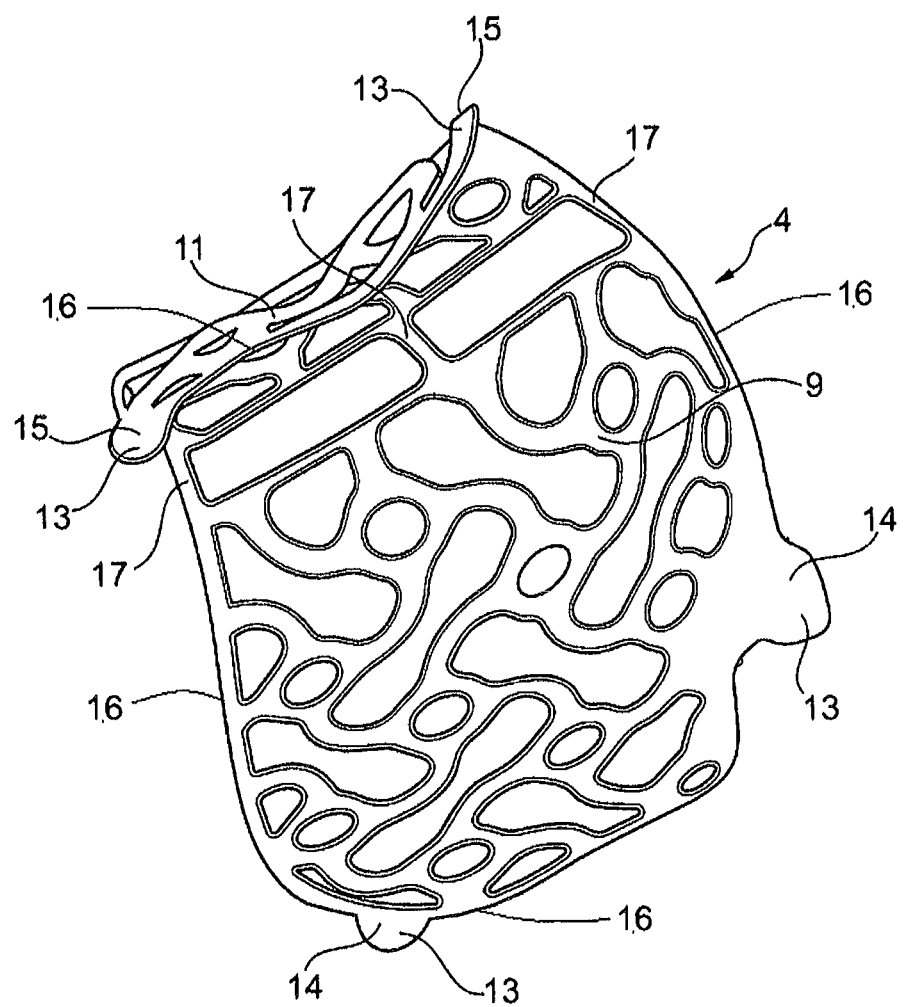
Figure 7:
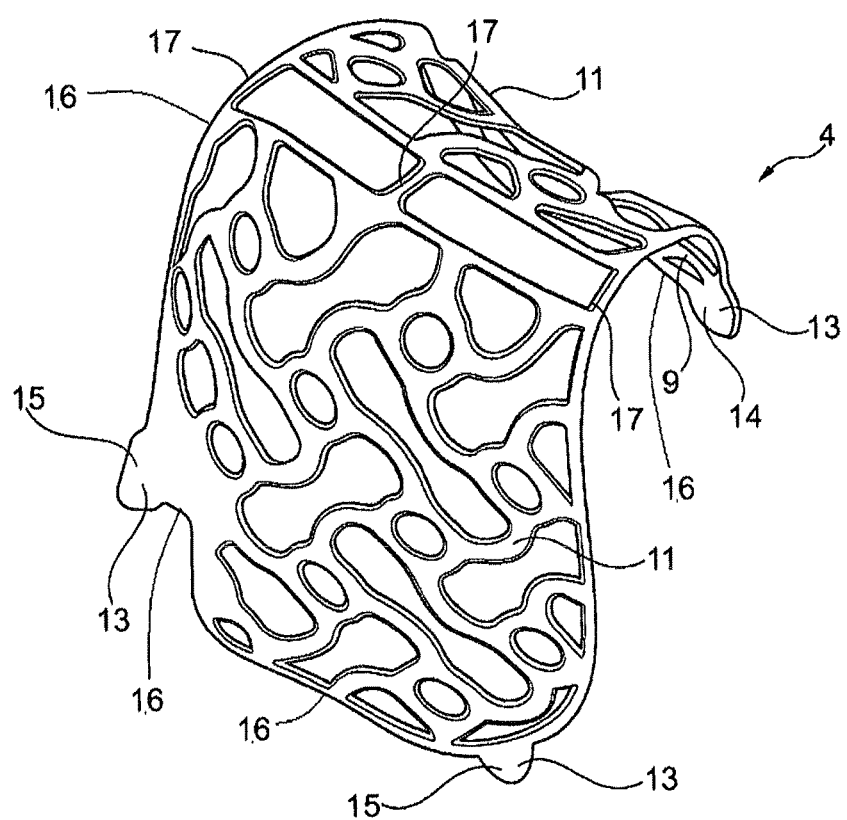
Figure 8:
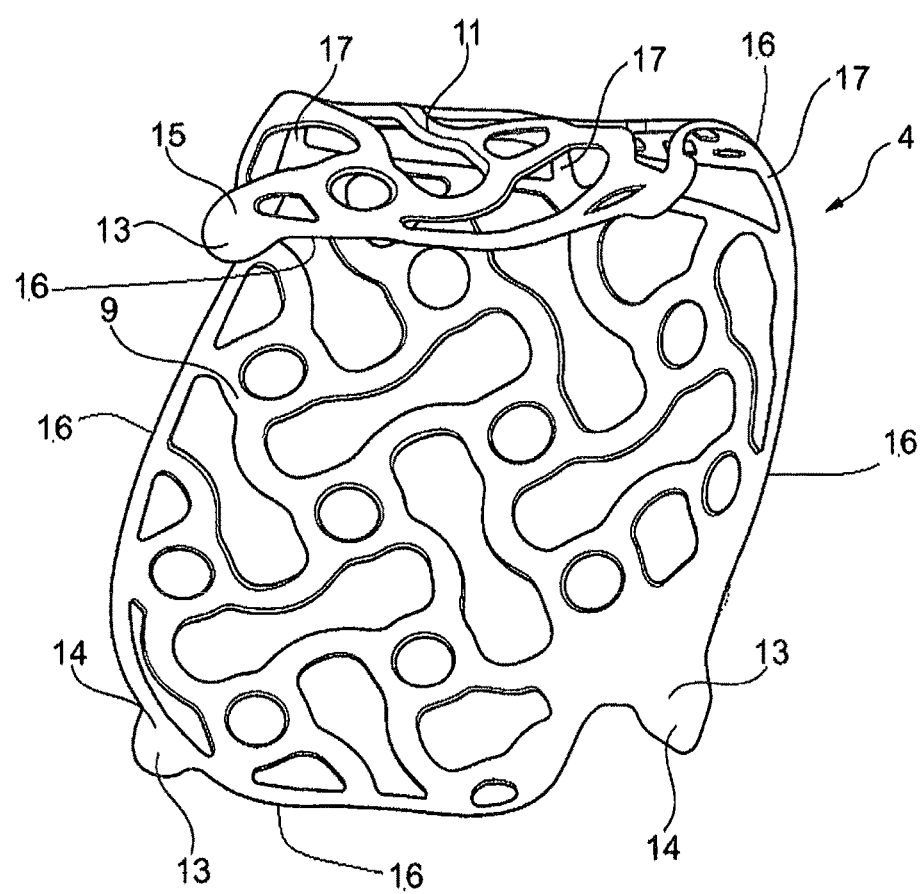
Figure 9:
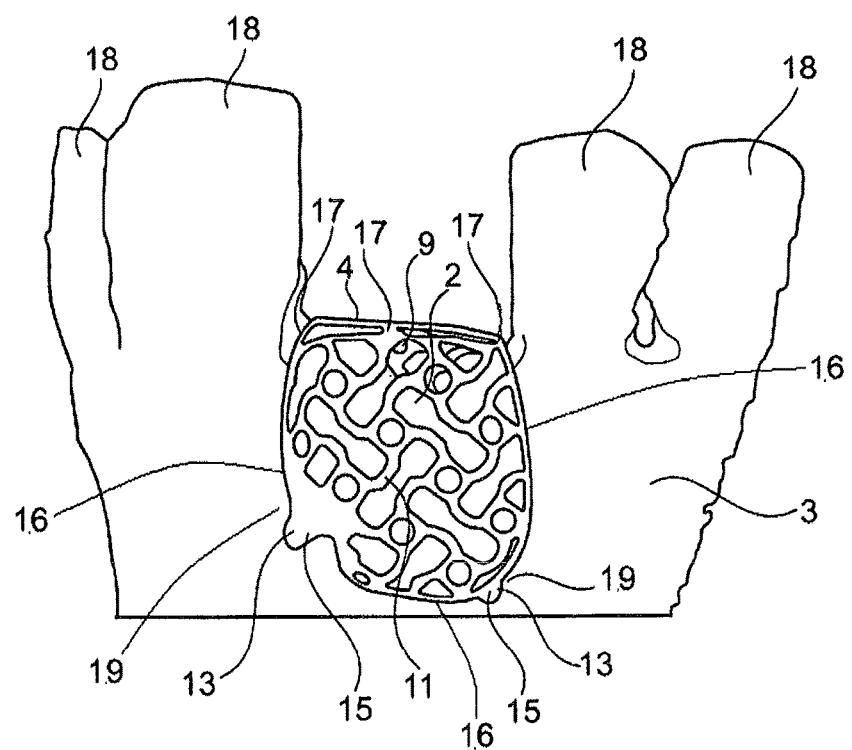

Exemplary embodiments of the object of the invention are shown in the drawing and will be explained in greater detail below. The figures show:

FIG. 1 a representation of a device according to the invention for covering and/or reconstruction of a bone defect site, FIG. 2 a representation of a differently shaped device according to the invention for covering and/or reconstruction of a bone defect site, FIG. 3 a representation of a differently shaped device according to the invention for covering and/or reconstruction of a bone defect site, FIG. 4 a representation of a differently shaped device according to the invention for covering and/or reconstruction of a bone defect site, FIG. 5 a detail of a cap, FIGS. 6 to 8 different representations of a cap having positioning means, and FIG. 9 a cap disposed at a bone defect site.

DESCRIPTION OF THE EXEMPLARY EMBODIMENTS

FIG. 1 shows a representation of a device 1 according to the invention for covering and/or reconstruction of a bone defect site 2 (bone defect) of a bone, particularly of a jawbone 3. The device 1 consists of a cap 4, which has one layer, and a fixation means 5, which, shown as a pin in FIG. 1, is disposed in the bone defect site 2 in order not to injure the healthy bone that borders on the bone defect site 2. Of course, it is also conceivable that multiple fixation means 5 are used for fixation of the cap 4, wherein these means would also be disposed in the bone defect site 2. The cap 4 is composed of a dimensionally stable material, so that it is self-supporting and no additional support is required. For fixation of the cap 4 (molded shell, rigid shell), the fixation means 5 is pushed into the cap 4 through a bore 6, and subsequently introduced into the bore 7 that is disposed in the jawbone 3. Subsequent fixation of the cap 4 preferably takes place by way of ultrasound welding. In ultrasound welding, an ultrasound generator preferably generates a precisely defined frequency, which is bundled by way of a sonotrode. After the resorbable fixation means 5 (pin) has been set onto a borehole (bore 7) that has been pre-drilled in the bone, a vibration that has been generated ensures liquefaction of the pin surfaces at its edges, thereby bringing about sliding of the pin into the borehole. By means of the change in the aggregate state, the pin penetrates even into the osseous cavities that cannot be reached by a conventional bone screw, so that great initial strength is achieved. Furthermore, the pin head unites with the cap 4 and ensures a stable, three-dimensional construct by means of a blocking mechanism. In ultrasound welding, the fixation means 5 is therefore plasticized, so that it unites with the jawbone 3 and the cap 4. As a result of the cap 4 that is fixed in place, a sealed interior 8 is formed between the jawbone 3 and the cap 4, which space is filled by means of regeneration of the bone and/or by means of introduction of a material of organic and/or inorganic origin, which can also be an autogenic, syngenic, allogenic, xenogenic, synthetic and/or alloplastic material, so that the regenerated bone or the introduced material corresponds to the shape of the first side 9 of the single-layer cap 4 that faces the bone defect site 2. In order to accelerate the regeneration process of the jawbone 3, the first side 9 of the cap 4 that faces the bone defect can have a surface conditioning (for example a microstructuring, pores, osteoblast attractants, means for promoting bone growth and/or bone replacement material that contains BMP).

FIG. 2 shows a representation of a differently shaped device 1 according to the invention for covering and/or reconstruction of a bone defect site 2 (bone defect) of a bone, particularly of a jawbone 3. In this figure, the gums 10 are additionally indicated.

FIG. 3 shows a representation of a differently shaped device 1 according to the invention for covering and/or reconstruction of a bone defect site 2 (bone defect), particularly of a jawbone 3. In this figure, the cap 4 is formed as a molded body, for example from human or animal bone, and has a first side 9 that faces the bone defect, which first side is adapted to the relief of the bone defect site 2, and a second side 11 that faces away from the bone defect, which second side corresponds to the shape of the regenerated bone.

FIG. 4 shows a representation of a differently shaped device 1 according to the invention for covering and/or reconstruction of a bone defect site 2 (bone defect) of a bone, particularly of a jawbone 3. In this figure, the cap 4 is formed as a molded body, for example of human or animal bone, and has a first side 9 that faces the bone defect and a second side 11 that faces away from the bone defect, which second side corresponds to the shape of the regenerated bone. An interior 8 is situated between the first side 9 and the bone defect site 2, which interior is filled by means of regeneration of the bone and/or by means of introduction of autogenic, syngenic, allogenic, xenogenic, synthetic and/or alloplastic material.

FIG. 5 shows a detail of a cap 4, the first side 9 of which, facing the bone defect, has openings 12, thereby forming a net-like structure.

FIGS. 6 to 8 show different representations of a cap 4, which has a first side 9 that faces a bone defect site and a second side 11 that faces away from the bone defect site, with positioning means 13 disposed at the rim 16 of the cap 4, which means have a side 14 that faces the healthy bone and a side 15 that faces away from the healthy bone. The positioning portion 13 includes a continuous wall. In the case of proper placement of the cap 4 at the bone defect site, which site is supported by the positioning means 13, the sides 14 that face a healthy bone touch the healthy bone, and thereby the positioning means 13 guarantee a perfect seat of the cap 4, if applicable even without placement of at least one fixation means not shown in FIGS. 6 to 8, or at least until at least one fixation means is disposed on the bone defect site. In order to be able to easily remove the cap 4 after bone regeneration, this cap has planned breaking points 17, and thereby it can be divided into two parts after the planned breaking point has been severed, in order to remove it.

FIG. 9 shows a cap 4 disposed at a bone defect site 2 of a jawbone 3, of which details are shown, which bone has teeth 18. As a result, it becomes evident that the cap 4 is preferably disposed only in the region of the bone defect site 2 of the jawbone 3, so that it neither spans nor touches a healthy bone 19. Therefore only the positioning means 13 disposed on the cap 4 have contact with the healthy bone 19.

In FIGS. 6 to 9, a cap 4 is shown, the first side 9 of which, facing the bone defect, corresponds to the shape of the regenerated bone. It is also conceivable that the positioning means 13 are disposed directly on the cap 4, in such a manner that its second side 11 that faces away from the bone defect corresponds to the shape of the regenerated bone. This could be brought about, for example, by means of placement of the positioning means 13 on the second side 11 of the cap 4 that faces away from the bone defect.

All of the characteristics represented here can be essential to the invention both by themselves and in any desired combination with one another.

REFERENCE NUMBER LIST 1 device
2 bone defect site
3 jawbone
4 cap 5 fixation means
6 bore
7 bore
8 interior
9 wall
10 gums
11 wall
12 opening
13 positioning means
14 wall
15 wall
16 rim
17 planned breaking point
18 tooth
19 healthy bone

The invention claimed is:

1. Device for a bone defect site, the device comprising:
a cap comprising a rim and a first side configured to face away from the bone defect and a second side configured to face toward the bone defect,
wherein the cap comprises a dimensionally stable material, and the second side of the cap or the first side of the cap is configured to correspond to the shape of a regenerated bone,
wherein
the device has at least one positioning portion having a continuous wall configured to face a healthy bone that borders on the bone defect, the at least one positioning portion being disposed at the rim of the cap,
or
the device has at least one connector for fixation of the cap within the region of the bone defect, and the device has at least one positioning portion having a wall configured to face a healthy bone that borders on the bone defect, the at least one positioning portion being disposed at the rim of the cap.

2. Device according to claim 1, wherein at least one member selected from the group consisting of the cap, the at least one connector, and the at least one positioning portion comprises, at least in part, a biocompatible material.

3. Device according to claim 2, wherein the material of the at least one member selected from the group consisting of the cap, the connector, and the at least one positioning portion is of organic or inorganic origin.

4. Device according to claim 1, wherein at least one member selected from the group consisting of the cap, the at least one connector, and the at least one positioning portion comprises, at least in part, a biodegradable material.

5. Device according to claim 1, wherein at least one member selected from the group consisting of the cap, the at least one connector, and the at least one positioning portion comprises, at least in part, a resorbable material.

6. Device according to claim 1, wherein at least one member selected from the group consisting of the cap, the at least one connector, and the at least one positioning portion comprises, at least in part, a polymer or a polymer compound.

7. Device according to claim 1, wherein at least one member selected from the group consisting of the cap, the at least one connector, and the at least one positioning portion comprises, at least in part, polylactide.

8. Device according to claim 1, wherein at least one member selected from the group consisting of the cap and the at least one positioning portion has a varying wall thickness.

9. Device according to claim 8, wherein the wall thickness amounts to at least 0.2 mm.

10. Device according to claim 1, wherein the connector comprises at least one member selected from the group consisting of a pin, a screw, a nail, and a bone adhesive.

11. Device according to claim 1, wherein the cap has at least one milling.

12. Device according to claim 11, wherein the milling corresponds with the connector.

13. Device according to claim 1, wherein the second side has a surface conditioning.

14. Device according to claim 13, wherein the surface conditioning has at least one member selected from the group consisting of a micro-structuring, pores, osteoblast attractants, a bone growth promoter, and bone replacement material that contains BMP.

15. Device according to claim 1, wherein the cap has at least one opening.

16. Device according to claim 1, wherein the cap has at least one planned breaking point.

17. Device according to claim 1, wherein the cap has at least one attachment device for at least one implant to be set.

18. Device according to claim 17, wherein the at least one attachment device is covered, at least in part, by a part of the cap that is connected with the remaining part of the cap via at least one planned breaking point.

19. Device according to claim 1, wherein a planned breaking point is disposed between the cap and the at least one positioning portion.

20. Method for production of a cap of a covering device for a bone defect site, comprising the following method steps:
recording of a first data set that represents the affected bone defect site in the actual state,
comparison of the first data set with a second data set, which represents the reference state of a bone regenerated at the bone defect site, wherein the second data set is produced via calculation or was recorded at a time when the bone at the site now to be regenerated was still a healthy bone,
use of the first data set and of the second data set for planning of the cap, which has a rim and a first side that faces away from the bone defect and a second side that faces the bone defect, thereby making it possible for the cap to be disposed exclusively in the region of the bone defect site, and to be fixed in place on a bone,
conversion of the planning of the cap to a planning data set, and
provision of the planning data set to a manufacturing method, in which the cap is formed from a dimensionally stable material, and the first side or the second side corresponds to the shape of the regenerated bone in the reference state, wherein during manufacturing of the cap, at least one positioning portion is disposed at the rim of the cap, and serves for positioning of the cap on a healthy bone that borders on the bone defect site, wherein the at least one positioning portion has a positioning device first wall that faces away from the healthy bone and a positioning device second wall that faces the healthy bone and corresponds to the healthy bone, at least in part.

21. Method according to claim 20, wherein
recording of the first data set represents the affected bone defect site in its three-dimensionality, or
recording of the second data set represents the shape of the bone that is still healthy in its three-dimensionality, or
recording of the first data set represents the affected bone defect site in its three-dimensionality and recording of the second data set represents the shape of the bone that is still healthy in its three-dimensionality.

22. Method according to claim 20, wherein recording of at least one of the first data set and the second data set takes place via at least one imaging method.

23. Method according to claim 20, wherein recording of at least one of the first data set and the second data set take(s) place using at least one method that allows three-dimensional representation of a bone.

24. Method for production of a cap according to claim 20, wherein recording of the data set of the healthy bone takes place after the healthy bone has grown out.

25. Method for production of a cap according to claim 24, wherein the data set of the healthy bone is stored on a memory medium for later use.

26. Method for production of a cap according to claim 20, wherein during the manufacturing process, the cap is formed via milling.

27. Method for production of a cap according to claim 20, wherein during manufacturing of the cap, at least one attachment device for at least one implant to be set is disposed on the cap.

28. Method for production of a cap according to claim 27, wherein at least one attachment device is exposed by removal of a part of the cap, which is connected with the remaining part of the cap via at least one planned breaking point before removal.

29. Method for production of a cap according to claim 20, wherein during manufacturing of the cap, at least one planned breaking point is disposed on the cap.

30. Method for production of a cap according to claim 20, wherein at least one planned breaking point is disposed between the cap and the at least one positioning portion.

31. Method for production of a cap according to claim 20, wherein at least one of a cleaning process and a sterilization process is carried out during manufacturing of the cap.

32. Method for production of a cap according to claim 20, wherein the cap can be used in at least one member selected from the group consisting of a device for covering of a bone defect site, a device for reconstruction of a bone defect site, and a device for covering and reconstruction of a bone defect site.

* * * * *